United States Patent [19]

Refojo

[11] 4,452,776

[45] Jun. 5, 1984

[54] HYDROGEL IMPLANT ARTICLE AND METHOD

[75] Inventor: Miguel F. Refojo, Lexington, Mass.

[73] Assignee: Eye Research Institute of Retina Foundation, Boston, Mass.

[21] Appl. No.: 357,735

[22] Filed: Mar. 12, 1982

Related U.S. Application Data

[63] Continuation-in-part of Ser. No. 67,630, Aug. 20, 1979, abandoned.

[51] Int. Cl.$^3$ .............. A61K 31/78; C08L 31/00; C08F 120/26
[52] U.S. Cl. ...................... 424/81; 264/2.5; 264/2.6; 264/2.7; 523/106; 523/111; 523/113; 524/559; 524/833; 526/320; 604/891; 604/893; 428/78
[58] Field of Search ............... 526/320; 524/559, 833; 523/106, 113, 111; 604/891, 893; 424/81; 264/2.5, 2.6, 2.7

[56] References Cited

U.S. PATENT DOCUMENTS

| 3,503,942 | 3/1970 | Seiderman | 526/232.1 |
|---|---|---|---|
| 3,566,874 | 3/1971 | Shepherd et al. | 424/81 |
| 3,575,946 | 4/1971 | Chromecek et al. | 200/29.6 H |
| 3,765,414 | 10/1973 | Arlen | 3/1 |
| 3,784,540 | 1/1974 | Kliment et al. | 526/320 |
| 3,857,932 | 12/1974 | Shepherd et al. | 424/81 |
| 3,868,447 | 2/1975 | Kliment | 424/81 |
| 3,892,721 | 7/1975 | Gustafson | 526/320 |
| 3,896,806 | 7/1975 | Wichterle | 128/260 |
| 3,906,087 | 9/1975 | Sim et al. | 424/81 |
| 3,951,528 | 4/1976 | Leeds | 526/320 |
| 3,983,083 | 9/1976 | Kaetsu et al. | 526/240 |
| 4,056,496 | 11/1977 | Mancini et al. | 260/29.6 TA |
| 4,111,922 | 9/1978 | Beede et al. | 526/292 |
| 4,113,686 | 9/1978 | Holcombe | 260/29.6 TA |
| 4,143,017 | 3/1979 | Tarumi et al. | 260/29.7 H |
| 4,145,511 | 3/1979 | Gilles | 528/73 |
| 4,163,092 | 7/1979 | Steckler | 526/292 |
| 4,180,308 | 12/1979 | Mancini et al. | 526/273 |
| 4,206,294 | 7/1980 | Simms | 525/242 |
| 4,224,427 | 9/1980 | Mueller et al. | 526/320 |
| 4,228,269 | 10/1980 | Loshaek et al. | 526/260 |
| 4,279,795 | 7/1981 | Yamashita et al. | 525/303 |

FOREIGN PATENT DOCUMENTS 46-41472 12/1971 Japan .................. 524/833
1495043 of 1974 United Kingdom .

OTHER PUBLICATIONS

Calabria et al., Archives of Ophthalmology, May, 1970, vol. 83, pp. 613–618 and Jul. 1971, vol. 86, pp. 77–81.
M. F. Refojo et al., "Ophthalmic Surgery", Dec. 1978, vol. 9, No. 6, 43–50.
M. F. Refojo, "International Ophthalmology Clinics," Spring 1973, vol. 13, No. 1, pp. 263–277.
M. Refojo, "Encyclopedia of Polymer Science and Technology," Supl. vol. 1, pp. 195–219.
M. Refojo, Encyclopedia of Chemical Technology, vol. 6, 3rd Edit., pp. 725–742.
M. Reuben, Clinical and Applied Technology, Publ. by John Wiley and Sons, Chapter 3, pp. 19–38.

Primary Examiner—Herbert J. Lilling
Attorney, Agent, or Firm—Lahive & Cockfield

[57] ABSTRACT

A hydrogel implant article of significant softness, pliability and elasticity when dry as well as when wet consists of a random cross-linked copolymer of 2-hydroxyethyl acrylate and an alkyl acrylate. The acrylate hydrogel article is useful, in one instance, as the material to produce a scleral buckle in retinal detachment surgery.

10 Claims, No Drawings

HYDROGEL IMPLANT ARTICLE AND METHOD

REFERENCE TO RELATED APPLICATIONS

This application is a continuation-in-part of copending U.S. application Ser. No. 67,630 filed Aug. 20, 1979 now abandoned entitled Hydrogel Implant Article and Method, the disclosure of which is incorporated herein by reference.

BACKGROUND OF THE INVENTION

This invention relates to a new scleral buckle material and more generally to a new synthetic hydrophilic polymer for eye surgery and other in vivo implants.

Synthetic materials have several applications in ophthalmic medicine, including surgical implantation to create a scleral buckle to correct a condition known as retinal detachment, and as contact lenses. Silicone materials, both rubber and sponge, are known for use in scleral buckle procedures. Synthetic organic polymers with hydrophilic properties also have been used as scleral buckle materials, and certain species are the popular materials for contact lenses. Recent developments in correcting retinal detachment with scleral buckling are described in "Sutureless Scleral Buckling", G. A. Calabria, R. C. Pruett, M. F. Refojo, and C. L. Schepens, *Archives of Ophthalmology*, May 1970, Vol. 83, pp. 613–618; "Further Experience With Sutureless Scleral Buckling Materials", G. A. Calabria, R. C. Pruett, and M. F. Refojo, *Archives of Ophthalmology*, July 1971, Vol. 86, pp. 77–81; and "Experimental Scleral Buckling With A Soft Xerogel Implant", M. F. Refojo and H. S. Liu, *Ophthalmic Surgery*, December 1978, Vol. 9, No. 6, pp. 43–50. Materials for contact lenses, and particularly for soft contact lenses, are described in "Contact Lens Materials", M. F. Refojo, *International Ophthalmology Clinics*, Spring 1973, Vol. 13, No. 1, pp. 263–277; "Contact Lenses", M. Refojo, *Encyclopedia of Polymer Science And Technology*, Supplement Volume 1, pp. 195–219; and "Contact Lenses", M. F. Refojo, *Encyclopedia of Chemical Technology*, Volume 6, Third Edition, pp. 720–742. The polymer chemistry of certain synthetic hydrogels is described in *Soft Contact Lenses: Clinical And Applied Technology*, M. Ruben, Editor, Published by John Wiley & Sons, Chapter 3, pp. 19–38.

Materials for these ophthalmologic applications are to be non-toxic and otherwise tolerated without causing tissue inflammation or other rejection mechanisms, and they are to be relatively nonabsorbable. The materials are also to be capable of sterilization without deterioration, and are to be permeable to oxygen, water and low molecular-weight water-soluble substances. Implant materials also are often to be non-biodegradable. Another desired property is that the implant material be capable of being cast or otherwise formed into an article of specific configuration, which the article retains. In addition, material for a scleral buckle preferably is soft, pliable and elastic; a specific objective is that it be capable of being compressed by overlying sutures without cutting through the implant or of being applied with sutureless techniques. Materials for ophthalmic surgery in addition are often desired to absorb antibiotics and other drugs for prolonged release after surgical implantation. In addition, it is desired that surgically implantable materials have pores of such small size that they do no form sites for infection by bacteria or other pathogens.

Known materials meet numerous of these properties, but all too often the fulfillment of some properties is attendant with deficiencies with regard to other properties. For example, methacrylate hydrogels known for use as scleral buckles have the disadvantage of being hard and stiff when dry; they become soft and pliable only when wet. The known silicone rubber sponges used in scleral buckle surgery is considered to have pores sufficiently large to provide a site for bacterial infection.

It is accordingly an object of this invention to provide an improved hydrophilic gel, or hydrogel, for in vivo implantation. "Implantation" and "implant" are used in this application in a broad context to include not only surgical implants but also a topical implant such as a contact lens.

A more particular object is to provide an implant hydrogel which attains the properties discussed above to a greater extent than previously available, and further to provide such a hydrogel suitable for ophthalmic use.

Another object of the invention is to provide an implant hydrogel having improved properties in terms of softness, in terms of elasticity, and in terms of resistance to tensile rupture. More specific objects are that the hydrogel be soft, pliable and elastic when dry as well as when wet, and furthermore that it be sufficiently tough, for example, to hold a surgical suture. Thus the objects of the invention include the provision of a scleral buckle hydrogel which is soft and elastic when wet as well as when dry, and which has sufficient resistance to tensile rupture to hold a suture.

It is also an object of the invention to provide a method for preparing hydrogel implant articles of the above character.

Other objects of the invention will in part be obvious and will in part appear hereinafter.

The invention accordingly comprises a composition of matter possessing the characteristics, properties and relation of constituents exemplified in the composition hereinafter described; the article possessing the features, properties, and relation of elements exemplified in the following detailed disclosure; and the several steps and the relation of one or more of such steps with respect to each of the others for the preparation of such a composition of matter and such an article; and the scope of the invention is indicated in the claims.

SUMMARY OF THE INVENTION

In accordance with the invention, it has been found that acrylate hydrophilic gels can be prepared with properties superior to those previously assumed. In particular, it was considered in the prior art that methacrylate hydrogels were preferred over those of acrylate derivatives. It is understood that this preference stemmed from the view that the methacrylate hydrogels were more resistant than acrylates to hydrolysis and to biodegradation, and were considered to have better stability and particularly resistance to thermodegradation, especially such as encountered in sterilizing with heat as in an autoclave. Contrary to this view, this invention provides acrylate hydrogels that function well as implants without exhibiting these supposed shortcomings and, further, that have advantages over prior materials.

The implant hydrogel which the invention provides is a copolymer consisting essentially of at least 35% by weight of alkyl acrylate, an amount up to about 65% by weight of 2-hydroxyethyl acrylate, and an amount up to about 5% by weight of a cross-linking agent. The monomers are polymerized by the solution polymerization technique, with simultaneous crosslinking, in an organic solvent, an example of which is ethylene glycol. A free radical initiator is also present in the prepolymer solution. Examples of the free radical initiator are isopropyl percarbonate, benzoyl peroxide, and azobisisobutyronitrile. Practice of the invention is not limited to such an initiator, and can for example instead use a redox catalyst, such as mixtures of ammonium persulfate and sodium metabisulfate. Typical cross-linking agents are ethylene glycol diacrylate, ethylene glycol dimethacrylate, di-or triethylene glycol diacrylates and divinyl benzene. Sufficient cross-linking agent may be present as an impurity in the 2-hydroxyethyl acrylate or alkyl acrylate monomers, especially in the 2-hydroxyethyl acrylate. The quantity of cross-linking agent present in the monomer can be determined in advance with standard techniques such as chromatography, and an appropriate additional quantity introduced prior to polymerization as needed. Increasing the amount of cross-linking agent present in the prepolymer solution serves to increase the Shore Durometer (Type A-2) hardness of the hydrogel. Typically, the cross-linking agent is present in an amount from 0.2% to as much as 4% of the volume of hydroxyethyl acrylate monomer.

The hydrogel implant polymerized from these monomers has the following formula in each cross-linked copolymer

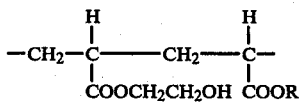

where R is an alkyl group, typically of up to four or five carbon atoms. The alkyl acrylate hence, in most instances at least, is selected from methyl acrylate, ethyl acrylate, propyl acrylate, butyl acrylate, pentyl acrylate, and isomers thereof. In accordance with the invention, the preferred alkyl acrylate is methyl acrylate.

A preferred method of preparing the implantable hydrogel which the invention provides includes the steps of placing a solution of the monomers with the selected initiator and selected cross-linking agent in a mold which in then sealed. The mold typically is siliconized glass tubing or of a plastic such as polyethylene or polypropylene. The prepolymer solution is frozen in dry ice in the mold, to remove gas, prior to sealing the mold closed. The monomers are polymerized in the mold at a controlled temperature of about 30° to 50° Centigrade for twelve to twenty-four hours. This is followed by curing in an oven at about 60° to 80° Centigrade for five to ten hours with a further, shorter, e.g. one hour, curing step at about 90° Centigrade. In one example, the polymerization is carried out by placing the mold in a water bath maintained at 37° Centigrade for twelve to fourteen hours, and the curing employs a first step at 70° Centigrade for seven hours and a second step at 90° for one hour.

Upon completion of the polymerization, including curing, the resultant hydrophilic gel copolymer is removed from the mold and treated to exchange the polymerization solvent and residual monomers as well as any other unpolymerized material, with an aqueous solution such as water or isotonic saline. Suitable solvents include methanol and ethanol. This washing and exchange typically includes a continuous extraction process and is continued until no measurable amount of leachable impurities remains in the copolymer. The resultant clean copolymer is sterilized by autoclaving, after which it typically is stored in isotonic saline or other physiological solution until ready for use.

The hydrogel obtained in the foregoing manner typically has a Shore Durometer (Type A-2) hardness whey dry in the range of ten to sixty-five with a typical and preferred value in the order of fifty-four. The acrylic hydrogel typically absorbs about 15% to 75% by weight of water or other aqueous solution, including drugs. In its hydrated state, the hydrogel typically has a Shore Durometer (Type A-2) hardness of up to 25 with a typical and preferred value in the order of ten.

The implant hydrogel thus is characterized by being soft, pliable and elastic both when wet with aqueous solution as well as when dry. These properties distinguish it from many hydrogel formulations known in the art which are soft, elastic and pliable when wet, but are significantly less so when dry. This advantage of the acrylate copolymer which the invention provides facilitates its use as an implant. For example, it facilitates implanting the hydrogel as a scleral implant in retinal detachment surgery.

The copolymer is also characterized by a pore size in the molecular range with maximum pore diameter in the order of twenty to thirty Angstrom units. Such sub-microscopic pores are desirable because they are too small to receive bacteria and like pathogens, while yet being sufficient to enable the hydrogel to absorb hydrophilic antibiotics or other aqueous drugs. An antibiotic typically is introduced by placing the hydrogel in an aqueous solution of the antibiotic shortly, e.g. one-half hour, before surgically implanting the hydrogel. The implanted hydrogel gradually releases the absorbed antibiotic over a relatively prolonged period after surgery, thereby minimizing the post-operative infection. Other features of the implant hydrogel are high tissue tolerance, stability under heat sterilization, stability against biodegradation after surgical implantation, and relatively high tensile strength.

The nature of the invention and the objects it attains will now be described further with reference to detailed non-limiting examples of the foregoing practice.

EXAMPLE I

An implant of methyl acrylate copolymer for ophthalmic surgical implantation containing approximately 33% by weight of 2-hydroxyethyl acrylate (HEA) and approximately 66% by weight of methyl acrylate (MA) was prepared as follows. Commercial grades of MA and of HEA were redistilled and analyzed by gas chromatography. The MA was determined to be pure, and the HEA contained (by volume) 0.6% acrylic acid, 1.0% ethylene glycol, and 1.2% ethylene glycol diacrylate. The redistilled monomers were mixed in the following proportions in six milliliters ethylene glycol as a solvent: HEA, 3 milliliters, and MA, 7 milliliters; plus 12 to 14 milligrams of isopropyl percarbonate as a polymerization initiator, i.e. free radical initiator. The 1.2% ethylene glycol diacrylate present in the distilled HEA monomer was sufficient to function as a crosslinking agent. To polymerize the mixture, the solution was placed in a mold of polypropylene tubing having a wall thickness of one millimeter and an inner diameter of six millimeters, and the tubing ends sealed after the liquid was frozen to remove gas bubbles. The sealed tube was placed in a water bath, and the polymerization reaction carried out for about twelve hours at 37° Centigrade, followed by a first curing step of seven hours in an oven at 70° Centigrade, and a second curing step at 85° Centigrade for one further hour. The copolymer was removed from the mold and washed thoroughly in distilled water at room temperature for several weeks, with repeated changes of water. The copolymer was next extracted in a soxhlet with methanol until negligible amounts of extractables were detected spectrophotometrically. The methanol which the polymer absorbed was then exchanged with distilled water by placing the polymer in water which was repeatedly changed. The hydrated polymer has more uniform dimensions and hardness when it is dried after replacement of the methanol, and then rehydrated. The resultant hydrated polymer was placed for sterilization and storage in a glass vial with isotonic sodium chloride solution, and the sealed vial sterilized in a steam autoclave for twenty minutes at 120° Centigrade.

The physical properties and occular tolerance of the methyl acrylate copolymer implant prepared in this manner are as follows. The copolymer is insoluble, but swells in water and other solvents. At equilibrium swelling in water or in physiological saline solution, it absorbs about 15% by wet weight of the liquid, and is white, opaque, and soft having a hardness of 10 (Shore Durometer Hardness Type A-2). When dry, the copolymer implant is soft, pliable, elastic and optically transparent with a Durometer hardness of 54 (Shore Durometer Type A-2). The copolymer implant also absorbs hydrophilic antibiotics that are released upon implantation.

Ocular tolerance and irritation for the copolymer implant were studied in rabbits by ocular irritation tests with extractibles from the implant, and by implant tolerance tests in the anterior chamber and at the episclera. The ocular irritation tests revealed no ocular irritation or congestion during or after a test period of four days. There was no difference in appearance between the test eyes and the control eyes. With regard to ocular tolerance to implants, rabbit eyes with anterior chamber implants initialled revealed a localized fibrinous transudate covering the implant material but which cleared completely within forty-eight hours, after which the implant was seen over a normal iris with clear cornea. In eyes with episcleral implants, the conjunctiva initially revealed localized congestion but with no subsequent signs of irritation, and the cornea was clear and the conjunctiva congestion subsided within three days of the implant operation. Macroscopic examination of enucleated eyes revealed no inflammatory changes. Histologically, eyes with anterior chamber implants revealed normal corneal endothelium and normal smooth iris surface. Similarly, in those with episcleral explants, the underlying sclera and overlying conjunctiva appeared normal except for mild condensation of fibrous tissue around the implant.

The copolymer article was also surgically implanted in rabbits as a scleral buckle by suturing it over the sclera. Post-operative examination and eyes enucleated from animals at three weeks and at three months following the implant surgery revealed no evidence of infection, rejection, or cutting through the sclera in any eye. No biodegradation of an implant was apparent even after one year.

From these and other tests it was determined that the new alkyl acrylate implant is well tolerated by ocular tissues, has good resistance to sutures, and has ideal softness for scleral indentation in retina detachment surgery.

EXAMPLE II

In contrast to polymerizing methyl acrylate in essentially a two-to-one volume proportion to hydroxyethyl acrylate as in Example I, a hydrogel implant containing approximately 53% by weight HEA and approximately 46% by weight MA was prepared according to the invention using essentially equal volumes. For this example, the redistilled methyl acrylate and 2-hydroxyethyl acrylate monomers described in Example I, but each in 5 milliliter quantities, were mixed in solution with 5 milliliters of ethylene glycol to which 10.8 milligrams isopropyl percarbonate were added. Again, sufficient ethylene glycol diacrylate was present as an impurity. The solution was polymerized, cured and washed as in Example I. The resultant dried copolymer is transparent, pliable, strong and elastic, but with slow elastic recovery. The Durometer hardness when dry is 55 (Shore Durometer A-2). Upon rehydration, the polymer absorbs 30% water by volume and is transparent, very soft (Durometer hardness of 0.5 when hydrated without prior drying, and a somewhat higher value when dried and then rehydrated), and elastic.

EXAMPLE III

A butyl acrylate hydrophilic gel implant containing approximately 50% by weight HEA and 49% by weight n-butyl acrylate (BA) is prepared according to the invention with 5 milliliters HEA monomer, 6 milliliters BA monomer, 5 milliliters of ethylene glycol solvent, and 11.2 milligrams of isopropyl percarbonate initiator. The monomers are redistilled, and the solution polymerized, as in Example I, with curing and washing to remove residuals as also described with reference to Example I. The cross-linking agent is ethylene glycol diacrylate present at about 2% as an impurity in the HEA monomer. The resultant copolymer when dry is soft, transparent, elastic and sticky, with a Durometer hardness of 12. Upon hydration, the polymer is transparent with good tensile strength, absorbs 11.2% water by wet weight, and has a Durometer measure of 2.6.

EXAMPLE IV

Some crosslinked copolymers of HEA and of alkyl acrylates in accordance with this invention, when hydrated in water or in a physiological saline solution, are opaque or at least translucent. This is the case with the polymers obtained according to Examples I and III. For most implant applications, such as for scleral buckling in retinal detachment surgery, the optical properties of the implant are irrelevant. However, for contact lenses and for intraocular implants, transparency is of course essential. One problem of currently available hydrophilic soft contact lenses is that they are relatively eacy to break during normal use; thus a tougher hydrophilic contact lens material is desirable.

Some crosslinked copolymers of this invention have been found to have excellent optical properties as well as high resistance to rupture, which make them useful for the manufacture of hydrophilic contact lenses. Copolymers of this kind are given in Example II and in the following further example.

A methyl acrylate hydrophilic gel implant containing approximately 43% by weight HEA and 56% by weight MA is prepared according to the invention with 4 milliliters HEA, 6 milliliters MA, 5 milliliters of ethylene glycol solvent, and 10.76 milligrams of isopropyl percarbonate as polymerization initiator.

Polymerization and simultaneous crosslinking of the monomers were carried out under the same conditions as given in Example I. The resulting polymer was water washed, methanol extracted, rehydrated, and dried. Upon rehydration in distilled water, it yielded a transparent, elastic, strong, hydrophilic material of wet durometer 12.9 and hydration 19.8%. Hydrated in physiological saline solution (0.9% sodium chloride), the durometer reading was 13 and the hydration 17.9%.

The foregoing description and examples show that one can obtain hydrated alkyl acrylate copolymer implants with diverse degrees of softness and of elasticity by increasing the proportion of ethylene glycol diacrylate or adding other crosslinking agents to the prepolymer mixture. Nonlimiting examples of such agents include ethylene glycol dimethylacrylate, diethylene glycol diacrylates, triethylene glycol diacrylates, and divinyl benzene. The prepolymer mixture can have countless combinations and proportions of monomers, with different dilutions in ethylene glycol and other suitable solvents, nonlimiting examples of which include diethylene glycol and ethanol. The apparent materials of choice, however, include those described in the foregoing specific examples, and the preferred copolymer contains from 40% to 70% by weight methyl acrylate and from 30%–60% by weight of 2-hydroxyethyl acrylate.

The hydrogel implants prepared according to the foregoing examples are molded, or cast, in the desired configuration. The copolymer in addition can be cut to a selected size and shape. In each instance, the implant article elastically retains its shape, even after heat sterilization, as by autoclave.

The alkyl acrylate copolymer implant of the invention is considered to have several advantages over prior art materials and particularly over silicone sponge as currently used in the treatment of retinal detachment. These advantages include the finding that the alkyl acrylate implant, unlike silicone sponge, does not have macroscopic pores but rather has microscopic pores and hence reduces chances of infection. Other advantages are that the implant has molecular size porosity and is hydrophilic so that it can absorb aqueous antibiotics and other aqueous drugs and act as a depot for the sustained delivery of such absorbed drugs for protecting the surgical field against early postoperative infection. In addition, the new implant, like the prior art silicone sponge but unlike prior gelatin implants, is nonabsorbable. A further advantage is that the alkyl acrylate implant is soft when dry and softer when hydrated, so it can be implanted in the fully hydrated state to obtain the required buckle during surgery or implanted in the dehydrated state to obtain a higher buckle upon in situ hydration. In contrast to silicone rubber, the new implant material is not electrostatically charged and therefore does not attract lint and dust, which can obviously cause post-operative complications. A further advantage is that the alkyl acrylate implant is tolerated by ocular tissue as least as well as solid silicone rubber.

It will thus be seen that the implant of the invention provides a combination of a significant number of desired properties, and that the objects set forth above, among those made apparent from the preceding description, are efficiently attained. Since certain changes may be made in the above composition of matter, in the carrying out of the foregoing method of its preparation, and in the resultant implant article as set forth, without departing from the scope of the invention, it is intended that all matter contained in the above description be interpreted as illustrative and not in a limiting sense.

It is also to be understood that the following claims are intended to cover all of the generic and specific features of the invention herein described, and all statements of the scope of the invention which, as a matter of language, might be said to fall therebetween. Particularly, it is to be understood that in the appended claims ingredients or compounds recited in the singular are intended to include compatable mixtures of such ingredients wherever the sense permits.

Having described the invention, what is claimed as new and secured by Letters Patent is:

1. A shape-retaining hydrogel surgical implant article characterized by significant softness and pliability in both hydrated and dehydrated states having a Shore Durometer Type A-2 hardness of between about 10 and 65 when dry and up to about 25 when wet with aqueous solution, said surgical implant article comprising an organic-solution polymerized copolymer consisting essentially of about 35% to 70% by weight of alkyl acrylate, about 30% to 65% by weight of 2-hydroxyethyl acrylate and an effective amount up to about 5% by weight of a cross-linking agent.

2. The surgical implant article of claim 1 wherein said alkyl acrylate is selected from a group consisting of methyl acrylate, ethyl acrylate, propyl acrylate, butyl acrylate, pentyl acrylate, and isomers thereof.

3. The surgical implant article of claim 2 wherein said cross-linking agent is selected from a group consisting of ethylene glycol diacrylate, ethylene glycol dimethacrylate, diethylene glycol diacrylate, triethylene glycol diacrylate, divinyl benzene, and mixtures thereof.

4. The surgical implant article of claim 1 wherein the ratio of alkyl acrylate to 2-hydroxyethyl acrylate is about 2:1 by weight.

5. The surgical implant article of claim 1 wherein the ratio of alkyl diacrylate to 2-hydroxyethyl acrylate is approximately 1:1 by weight.

6. The surgical implant article of claim 1 wherein said alkyl acrylate and said 2-hydroxyethyl acrylate are polymerized in an ethylene glycol solution.

7. The surgical implant article of claim 1 further comprising an antibiotic.

8. An improved method of surgical implantation wherein the improvement comprises the step of selecting as the implant the hydrogel article of claim 1.

9. A method as set forth in claim 8 wherein said improvement includes selecting said alkyl acrylate from the group thereof consisting of methyl acrylate, ethyl acrylate, propyl acrylate, butyl acrylate, and pentyl acrylate and isomers thereof.

10. A method of preparing a shape-retaining implant article characterized by significant softness and pliability in both hydrated and dehydrated states having a Shore Durometer type A-2 hardness of between about 10 and 65 when dry and up to about 25 when wet with aqueous solution, said article comprising a copolymer consisting essentially of at least 35% by weight of alkyl acrylate, an amount up to about 65% by weight of 2-hydroxyethyl acrylate and an effective amount up to about 5% by weight of a cross-linking agent, said method comprising the successive steps of A. mixing 2-hydroxyethyl acrylate and an alkyl acrylate in a water-soluble organic solvent with a cross-linking agent and with a free radical initiator, B. placing said solution in a sealed mold, C. subjecting the monomers to solution polymerization and crosslinking in said mold under controlled temperature, D. curing the copolymer in the mold, E. removing the resultant copolymer from the mold, and F. extracting residues and solvent from said copolymer.

* * * * *